United States Patent [19]

Demaray

[11] 4,270,381
[45] Jun. 2, 1981

[54] RECORDING INSTRUMENT TO MEASURE MICROBAL GAS PRODUCTION

[76] Inventor: David E. Demaray, NW. 140 Windrus St., Pullman, Wash. 99163

[21] Appl. No.: 80,513

[22] Filed: Oct. 1, 1979

[51] Int. Cl.³ .................. C12Q 1/00; G01D 9/00; G01N 7/00
[52] U.S. Cl. .................................. 73/19; 73/149; 346/72; 435/4
[58] Field of Search .............. 73/421.5 R, 19, 149; 346/72; 435/4

[56] References Cited

U.S. PATENT DOCUMENTS

| | | | |
|---|---|---|---|
| 890,844 | 6/1908 | Connet | 346/72 X |
| 2,038,044 | 4/1936 | Heald | 435/4 X |
| 2,768,523 | 10/1956 | Baker | 73/19 |
| 3,255,585 | 12/1965 | Wohnoutka | 60/262 |
| 3,387,487 | 6/1968 | Hodges, Jr. | 73/19 |
| 3,487,682 | 1/1970 | Whitehead, Jr. | 73/149 |
| 3,864,086 | 2/1975 | Geist et al. | 422/68 |

Primary Examiner—Daniel M. Yasich
Attorney, Agent, or Firm—Keith S. Bergman

[57] ABSTRACT

An instrument to accept multiple microbal samples and measure the gaseous products produced thereby as a function of time. Each sample module provides a closed reactional vessel communicating to a liquid reservoir from which displaced liquid passes to a vertical measuring column wherein it activates a float which moves a marker responsive to volume of gas produced in the reaction vessel. Plural sample modules are combined so that markers of all move in a parallel direction upon a recording sheet moved perpendicularly thereto to provide a record of gas formation as a function of time. The instrument is particularly adapted to measure the activity of a yeast activated fermentation process as in bread making.

5 Claims, 4 Drawing Figures

U.S. Patent Jun. 2, 1981 4,270,381
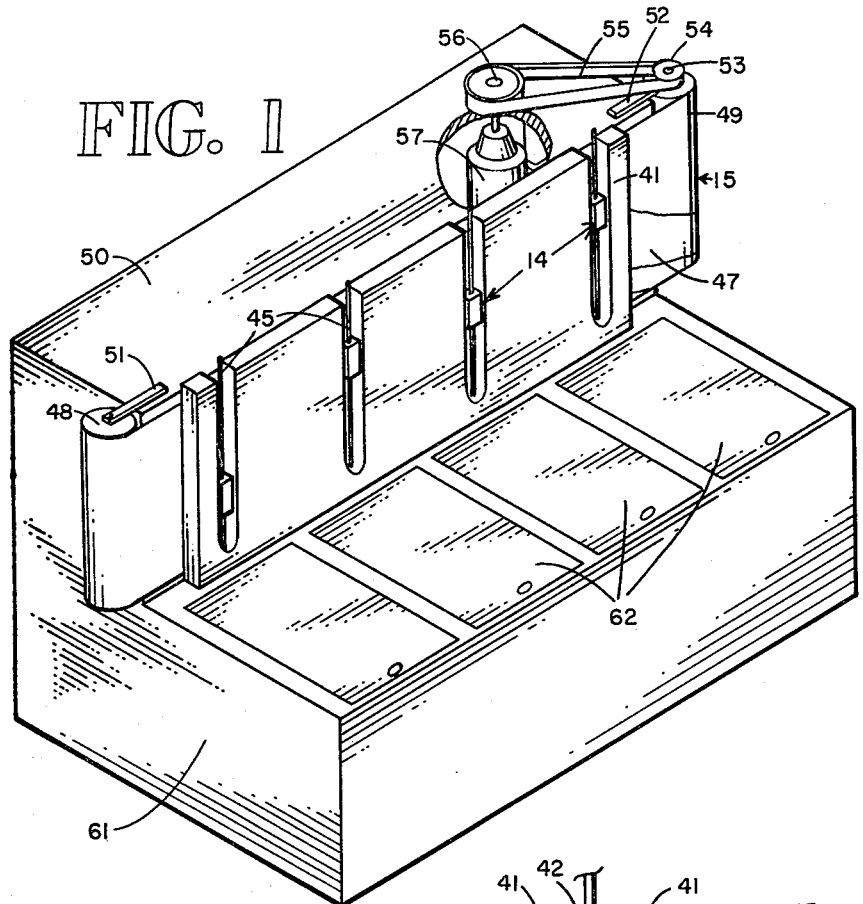
FIG. 1
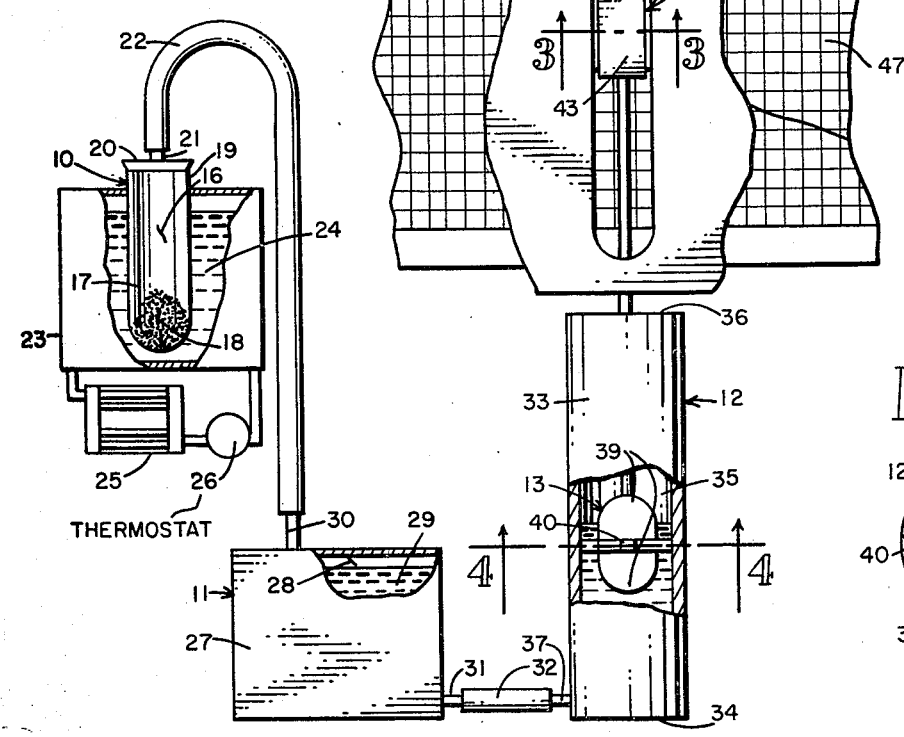
FIG. 2
FIG. 3
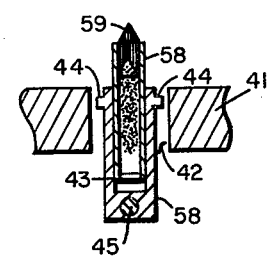
FIG. 4
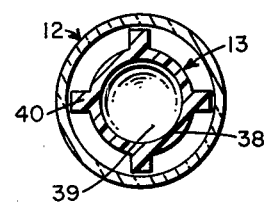

RECORDING INSTRUMENT TO MEASURE MICROBAL GAS PRODUCTION

BACKGROUND OF INVENTION

A. Related Applications

There are no applications related hereto heretofore filed in this or any foreign country.

B. Field of Invention

My invention provides an instrument to measure the gaseous products of metabolism of several microbal samples and particularly the volume of gas, as a function of time, produced by yeast fermentation.

C. Description of Prior Art

My invention is concerned generally with the measurement of gases produced by microbal metabolism and especially carbon dioxide produced in the yeast-flour fermentative process. This type of measuration is particularly important in materials testing and in determining process parameters in processes involving yeast, such as brewing and yeast production, as well as general microbal processes that produce gas.

Yeast metabolism, whether of the respiratory or fermentative type, produces carbon dioxide and commonly this is the only gaseous product of the metabolism, at least that is produced in any significant quantity. Because of this reaction a common method of measuring yeast activity has been to measure the volume of gas produced by a particular sample under pre-determined conditions over a period of time. This measure may then be used either absolutely or comparatively to determine the activity of the particular yeast or the nature of other process components or parameters. The common method of making this measurement in the past has been to use a typical laboratory bomb with an attached manometer of some sort. The process has been individualistic by nature, quite time consuming, a clumsy operation and generally has provided no automatic record of gas production as a function of time. The results oftentimes from tests made at different times have not been particularly constant or repeatable, apparently principally because of inconsistencies and inaccuracies that resulted from the laboratory nature of the process.

My invention seeks to solve these problems by providing a testing apparatus to record the gas production of individual microbal samples as a function of time. The testing apparatus may be adapted by combining sample modules to operate simultaneously on a plurality of samples. It provides a hydraulically activated recording mechanism that creates a continuous record of total volume of gas production over a period of time while former devices measured only such gas production at one or more discrete points of time. The record is commonly provided on paper by differentiable recording pens so that the trace from each sample may be readily distinguishable from that of another. The device provides temperature controls to maintain appropriate thermal environment for samples and does not raise gas pressure on the sample any more than would a normal vented manometer. The results obtained with the apparatus are substantially similar to those obtained with the non-recording bombs heretofore used for such purposes, but are quite consistent and repeatable.

SUMMARY OF INVENTION

My invention provides generally a measuring apparatus that accepts multiple microbal samples, maintains them in a controlled thermal environment, measures and continuously records the gaseous products of their metabolism.

The testing apparatus comprises plural similar modules each providing a closed sample container having a gas passageway communicating to a fluid reservoir with an overflow channel communicating to a vertical measuring cylinder which carries a vertically movable float mechanically interconnected with a recording pen to move that pen responsively to the float position and fluid level. A motor driven record sheet moves in a horizontal direction perpendicular to recording pen motion to record the pen trace indicating volume of gas produced by the microbal samples as a function of time. The sample container is maintained in a thermostatically regulated water bath to provide an appropriate thermal environ for the sample. Various recording pens may be provided with different colored inks to provide readily identifiable traces related to each individual sample. A plurality of these individual modules may be combined in a single instrument.

In providing such a measuring device it is:

A principal object of my invention to create apparatus to measure gas production of microbal samples and continuously record the total volume of gas produced as a function of time.

A further object of my invention to provide such apparatus that may have a plurality of similar, associated measuring modules to enable it to accept a plurality of individual samples and individually record the gas production of each.

A still further object of my invention to provide such apparatus that maintains an appropriate adjustable thermal environment for the microbal samples.

A still further object of my invention to provide such apparatus that is hydraulically or mechanically activated to avoid problems associated with electronic noise.

A still further object of my invention to provide such a testing device that is of new and novel design, of rugged and durable nature, of simple and economic manufacture and one otherwise well adapted for the uses and purposes for which it is intended.

Other and further objects of my invention will appear from the following specification and accompanying drawings which form a part of this application. In carrying out the objects of my invention, however, it is to be understood that its accidental features are susceptible of change in design and structural arrangement with only one preferred and practical embodiment being illustrated in the accompanying drawings as is required.

BRIEF DESCRIPTION OF DRAWINGS

In the accompanying drawings which form a part hereof and wherein like numbers of reference refer to similar parts throughout:

FIG. 1 is an isometric surface view of a multi-sample version of my invention showing its various parts, their configuration and relationship.

FIG. 2 is a more detailed, semi-diagrammatic, orthographic view of an individual module of my invention showing its parts, their inter-relationship and function.

FIG. 3 is a horizontal, cross-sectional view through the recording pen of FIG. 2, taken on the line 3—3 thereon in the direction indicated by the arrows.

FIG. 4 is a horizontal, cross-sectional view through the float mechanism of my invention, taken on the line 4—4 of FIG. 2 in the direction indicated by the arrows.

DESCRIPTION OF THE PREFERRED EMBODIMENT

As seen particularly in FIG. 1 my invention comprises a plurality of individual sample modules each providing sample container 10 having a gas passageway communicating to fluid reservoir 11 which in turn communicates for fluid passage to measuring cylinder 12. Float 13 is carried for vertical motion in the measuring cylinder and mechanically communicates with marker 14 to move the marker responsive to float position. Recorder 15 moves a recording sheet beneath markers 14 to provide a recorded trace of the vertical marker position which may be translated into the functional relationship of the volume of gas produced by a sample in relationship to time.

Sample container 10 provides gas-tight sample chamber 16, in the instance illustrated by means of cylindrical tube 17 having closed end 13 and open end 19. Open end 19 of the tube is closed by stopper 20 providing means of ingress and igress and carrying male fixture 21 for operative interconnection of gas tube 22. All of these elements are formed of some reasonably rigid material impervious to gas and such as does not absorb great quantities of gas within its structure. Commonly, tube 17 will be of laboratory glassware, stopper 20 of reasonably dense rubber and fixture 21 of metal such as stainless steel.

Commonly most gas producing microbal activity that is subjected to measurement is carried on in standardized environments, particularly as those environments are related to temperature and again, quite commonly, these desired temperature ranges are commonly different from generally prevailing temperatures in the environs of the measurement. Because of this it is convenient, though not necessary, to associate a thermally controlled water bath or some similar temperature controlling device with the sample containers. In FIG. 2 of the illustrations sample container 10 is partially submerged and substantially surrounded by fluid 24 carried in container 23. The temperature of this fluid is maintained by heating device 25 and adjustably controlled to pre-determined standard by associated thermostat 26, both interconnected in series with each other and with container 23 to allow circuitous passage of fluid 24 through the system. Commonly the temperatures desired in fluid 24 will be above those of the ambient atmosphere and if so, heat exchanger 25 will affirmatively provide heat to the system. If, perchance, temperatures lower than those of the ambient atmosphere are desired, a negative heating system or refrigeration unit will provide the desired result. The type of adjustable temperature water bath illustrated is well known in the biological and chemical arts and is not new per se. Obviously other temperature relating devices of a similar nature such as a sandbath, autoclave, refrigerator, incubator or the like may also serve the purposes of my invention.

Fluid reservoir 11 provides reservoir container 27 defining enclosed reservoir chamber 28 containing fluid 29. The upper portion of reservoir container 27 provides male input fixture 30 to accept one end of gas tube 22 and the lowermost portion of the reservoir provides male output fixture 31 to accept one end of fluid tube 32. The reservoir itself is preferably formed of some reasonably rigid material that is substantially impervious to both the gas and fluid that it is to contain, commonly a metal, glass or some high density laboratory type plastic. Both input and output fixtures 30, 31 should be of the same general nature as the reservoir container and in the instance illustrated, are of metal. Fluid 21 must be a substance substantially nonreactive with any gaseous products of microbal metabolism and should not absorb any substantial quantities of such gases. The fluid must also be stable at the temperature ranges involved and create a fairly low partial gas pressure of vapors that are not harmful to the biologic samples to be subjected to measurement. Generally water serves these purposes admirably, though in some of extreme temperatures it may be necessary to use some other type of fluid such as especially alcohol or fluid silicone.

Gas tube 22 and fluid tube 32 define internal channels somewhat the same size as the fixtures to which their ends are connected for passage of gas and fluid respectively. The materials from which these tubes are formed should be substantially impervious and non-reactive to the products they are to contain, neither should be particularly absorptive of the contained product and both preferably should be elastically resilient to allow attachment to fixtures. Ordinary rubber or plastic laboratory tubing serves these purposes of my invention admirably. The dimension of the tubing is not critical but its length should be appropriate to span the distances required and its diameter should be such as to permit free passage of products carried thereby.

Measuring cylinder 12 provides a vessel with generrally vertical, cylindrical sides 33 structurally communicating with flat bottom 34 to define measuring chamber 35 having open top 36 which may be partially but not completely closed, if desired, to prevent the entry of debris. The lowermost portion of vertical cylinder 33 carries male input fixture 37 to accept one end of fluid tube 32 in a nice fit. The dimensioning of measuring cylinder 12 is such that its vertical height is somewhat greater than the vertical height of fluid reservoir 11 and the volume of the measuring chamber should generally be slightly greater than the volume of the fluid reservoir. The orientation of the fluid reservoir and measuring cylinder relative each other is somewhat critical. Preferably the bottoms of the two will be co-planar but the top of the measuring cylinder will extend to a level that is at least slightly above the top of the fluid reservoir to prevent any overflow from the element.

Float 13 is a bulbous structure of some rigidity providing an external periphery adapting it to freely move vertically within measuring chamber 35. Preferably it is configured with medial portion 38 formed substantially as a cylinder with two similar, hemispherical ends 39. Medial cylindrical portion 38 carries annular guide 40 extending normally outwardly therefrom to nearly contact the internal surface of measuring cylinder 12 and thusly maintain the float in a medial position therein. The radially outer surface of annular guide 40 should be configured substantially similar to but slightly smaller than the cross-sectional shape of the chamber of measuring cylinder 12 to allow free vertical motion of the float within the measuring cylinder but yet maintain its axial alignment during this motion. To serve its purpose the float structure must be less dense than fluid 24 and preferably should be reasonably rigid. I prefer to form the float with a periphery of rigid plastic material defining an internal void that may be filled with gas or secondarily with a foam type plastic.

Marker structure 14 provides rigid marker guide 41 defining vertical elongate marker body slot 42. This slot slidably supports marker body 43 by some means of small guide projections 44 defined on each of the lateral sides of that body. Guide 41 is positionally maintained relative to measuring cylinder 12 to locate marker body slot 42 above, parallel to and immediately adjacent an upward extension of the axis of measuring cylinder as illustrated in FIG. 2. Relatively long, rigid marker connecting rod 45 communicates from the upper, medial part of float 13 to the marker rod body. Both float 13 and marker body 43 are rigidly attached to the marker connecting rod so as to maintain a constant distance therebetween and both the marker body and connecting rod must be free to move in the vertical dimension relative to their supporting structures.

Marker body 43 carries marker pen 58 in an appropriate medial channel. The pen carries marking fluid to produce a mark of some small dimension on a recording surface maintained at marker tip 59. The pen is positionally adjustable relative to body 43 by means of set screws 60 communicating therebetween to assure proper position for marking tape 47. The particular type of marking pen illustrated is known in the marking arts and is not new per se. Other types of marking devices such as a pencil, stylus or the like well may serve the purposes of my invention when associated with an appropriate recording surface.

Recorder structure 15 provides elongate paper tape 47 supported on supply roll 48 and collected on a driving roll 49. Rigid recorder housing 50 rotatably supports the supply roll axle in bearing structures 51 at one end and rotatably supports driving roll axle 53 in bearing structures 52 at the other end while providing a rigid backing or platen for tape 47 extending therebetween. The width of tape 47, that is its vertical dimension, is substantially as great as the possible vertical extension of marker structures 14.

Driving roll shaft 53 extends upwardly above the uppermost portion of bearing structure 52 to irrotatably carry pulley 54 communicating by belt 55 with driving pulley 56 carried and motivated by motor 57 supported within recorder housing 50 to provide a driving mechanism for the driving roll. Appropriate control structure (not shown) is associated with the motor to control it and preferably provide adjustable predetermined driving speeds to aid in interpreting records provided by the device. Recorder housing 50 is configured and dimensioned to provide an appropriate distance between supply roll 48 and driving roll 49 to accommodate the number of markers desired in a particular apparatus and the unit is so positionally related to the marker structure that markers will mark upon tape 47 as that tape is moved relative to the markers. This type of recorder structure per se is known in the testing and measuring arts and its details are therefore not specified with any great finesse.

Preferably for best operation, the forward surface (adjacent markers) of recording housing 50, marker guide 41 and measuring cylinder 12 are all angled rearwardly in their upper portions at an angle of approximately three and one-half degrees ($3\frac{1}{2}°$) to the vertical. This tends, because of gradational bias, to maintain a slight pressure of the marking pen on the recording tape carried against the forward surface of the recording housing and produces a better recording on the tape than would have been produced were all of the elements exactly vertically oriented.

One of the modules described provides analysis for a single microbal sample 18. Any number of such similar modules may be assembled in one individual testing apparatus to accommodate any desired number of samples. In the apparatus illustrated in FIG. 1, four such units have been combined. In such combinations it is generally convenient to provide some sort of base housing 61 to maintain the sample container, fluid reservoir, measuring cylinder and support the recorder housing as illustrated. If such a base structure is used it is most convenient to provide plural doors 62 in the base structure to cover and allow access to any individual sample unit, as desired. Any number of sample units may be assembled in a testing apparatus, but I have found eight to twelve such units to be a most convenient assemblage.

Having thusly described the structure of my invention its operation may be understood.

Firstly a multi-sample measuring apparatus is formed as specified. Predetermined quantities of the microbal mixture to be tested, normally determined by weight, are placed in the several sample containers 10, one sample in each container, and stoppers 20 are replaced to form a semi-anerobic chamber. The temperature of the water bath fluid 24 is adjusted by means of thermostat 26 to maintain the appropriate environment for the test, commonly with a yeast-flour type fermentative reaction approximately eighty degrees fahrenheit (80° F.). The device is then maintained in this condition for the desired test period.

During the test as the yeast metabolizes it will form carbon dioxide gas. This gas will form a partial pressure in the sample container and passageway connecting the sample container to the reservoir. When that pressure rises above the atmospheric pressure existing in the test environs, gas will pass into fluid reservoir 11 and cause some of the fluid contained therein to pass outwardly into measuring cylinder 12. In the null condition, because of the structure of the device, the vertical level of fluids in the reservoir and the measuring cylinder will be co-planar in a horizontal plane, but as fluid is moved out of the fluid reservoir by the gas pressure created in the sample container the level of water in the measuring cylinder will move upwardly from its null position. This in turn will cause float 13 to move vertically upwardly to move marker body 43 and marking pen 58 upwardly responsively to the volume of fluid displaced from the fluid reservoir. Tape 47 will be moving in a horizontal direction with marker pen 58 in marking contact with the surface of the tape to make a trace on the tape indicating the change in fluid volume of the reservoir as a function of time of passage of the tape. Since the volume of liquid displaced from the fluid reservoir is substantially proportionate to the volume of gas produced by the microbal sample and since the motion of the paper tape relative to the marking pen is a function of tape speed and thusly of time, the trace made by the pen on the marking tape represents a functional relationship of volume of gas production of the microbal sample to time. By methods well known in the measuration arts this functional relationship may be readily translated into common units of measure indicating volume of gas produced in any particular period of time and the total volume of gas produced during a lapsed period, both of which are common measures used to indicate the so-called "activity" of various microbal samples.

In the particular case of a yeast-flour fermentative type reaction the activity of one component may then be determined as compared to some fixed standard when the activity of the other components is known or maintained constant. This allows the common testing of either yeast or flour by using elements of known nature as a standard. The same type of measurement may be applied to many other reactions of various microbal agents that produce gas as a product of their metabolism or otherwise in the course of their activity.

It is to be noted that my invention is particularly useful for determining the activity of yeast activated fermentative processes, since these processes normally require a somewhat anerobic environment. Yeast metabolism of an oxidative nature may be measured with my invention but commonly to do so oxygen will have to be introduced into the sample chamber and to make any meaningful measurements its volume will have to be pre-determined under existing environmental conditions and allowance made therefore in determining the total volume of gas produced. Normally oxidative reactions are productive of much more gas (generally four times more) than fermentative reactions and volumes of various elements may have to be increased to accommodate this type of reaction. Generally, however, the fermentative type reaction is of much more commercial importance than the oxidative one.

It is to be particularly noted that since the trace made by any sample on the tape is a continuous representation of the functional relationship of the volume of gaseous products of metabolism and time, it is readily possible to determine the speed of the reaction at any point in time and also to determine the total amount of reaction prior to any particular period of time, either of which are oftentimes desired knowledge. It is to be further noted that generally this information cannot be gleaned from the bomb type apparatus heretofore known for such testing, at least without making a plurality of closely spaced individual observations which requires constant individual attendance, are time consuming and oftentimes quite inaccurate.

It is also to be noted that my entire system operates either on hydraulic or mechanical principles and does not have any electronic type measuring components. The apparatus is therefore completely unaffected by electronic transients or noise common in many testing environments.

It is further to be noted that normal testing procedures for yeast fermentative type reactions extend over substantial periods of time and that during this entire period of time, after initiation, my apparatus operates automatically and requires no personal attention.

The foregoing description of my invention is necessarily of a detailed nature so that a specific embodiment of it might be set forth as required, but it is to be understood that various modifications of detail, rearrangement and multiplication of parts might be resorted to without departing from its spirit, essence or scope.

Having thusly described my invention, what I desire to protect by Letters Patent, and what I claim is:

1. A measuring instrument to provide a continuous record of the gas production of at least one microbal sample as a function of time, comprising, in combination:

at least one sample container defining an enclosed chamber with means of ingress and egress thereto carrying a microbal sample and communicating for gas transmission with a fluid reservoir providing an enclosed chamber filled with fluid and communicating in its lowermost portion for fluid transmission with a vertical measuring cylinder having a vertical height and defining a contained volume greater than the vertical height and contained volume of said fluid reservoir and positioned with its uppermost part vertically above the uppermost part of the fluid reservoir;

a float carried for vertical motion in response to fluid variations within the measuring cylinder and mechanically communicating with a marker structure having a marking device movable responsive to the motion of the float by a mechanical linkage therebetween; and a recorder having a elongate tape movable perpendicularly to the motion of the marker and positioned in operative contact therewith to be marked upon by the marker to make a tracing upon the tape indicating the vertical position of the marker relative thereto.

2. The invention of claim 1 further characterized by:

the mechanical linkage between the float and the marker structure comprising an elongate, rigid rod structurally carried by the upper medial part of the float to extend thereabove; and immovably carry the marker at a spaced distance above the float with guide structure associated with the marker to aid in maintaining its alignment for vertical motion.

3. The invention of claim 1 further characterized by:

a water bath associated with the sample container to maintain the environment of a microbal sample at a predetermined temperature.

4. The invention of claim 1 further characterized by:

the vertical cylinder marker structure and recorder tape all having a similar rearward slope of approximately three and one-half degrees (3½°) from the vertical to create a gravity bias tending to maintain the marker pen in operative contact with the recorder tape.

5. A plurality of the inventions of claim 1 associated together in a common housing served by a single recorder with means to identify individual traces of the marker.

* * * * *